United States Patent [19]

LeSota

[11] Patent Number: 5,208,272
[45] Date of Patent: May 4, 1993

[54] MILDEW RESISTANT PAINT COMPOSITIONS COMPRISING AN ISOTHIAZOLONE AND A WATER-INSOLUBLE ZINC COMPOUND, ARTICLES, AND METHODS

[75] Inventor: Stanley LeSota, Horsham, Pa.

[73] Assignee: Rohm and Haas Company, Philadelphia, Pa.

[21] Appl. No.: 596,804

[22] Filed: Oct. 12, 1990

Related U.S. Application Data

[63] Continuation of Ser. No. 360,504, Jun. 2, 1989, abandoned.

[51] Int. Cl.$^5$ .................. A61K 31/78; G09D 5/16
[52] U.S. Cl. ...................................... 523/122; 524/723
[58] Field of Search ........................ 523/122, 723

[56] References Cited

U.S. PATENT DOCUMENTS

| | | | |
|---|---|---|---|
| 3,523,121 | 8/1970 | Lewis et al. | 260/302 |
| 3,761,488 | 9/1973 | Lewis et al. | 260/302 |
| 3,870,795 | 3/1975 | Miller et al. | 260/299 |
| 4,067,878 | 1/1978 | Miller et al. | 260/302 |
| 4,150,026 | 4/1979 | Miller et al. | 260/302 |
| 4,241,214 | 12/1980 | Miller et al. | 260/302 |
| 4,335,027 | 6/1982 | Cremeans et al. | 528/295.5 |
| 4,737,491 | 4/1988 | Leppavuori et al. | 514/184 |
| 4,783,221 | 11/1988 | Grove | 260/299 |
| 4,895,881 | 1/1990 | Bigner | 523/122 |
| 4,973,392 | 11/1990 | Gupta | 524/901 |

*Primary Examiner*—Thurman K. Page
*Assistant Examiner*—Peter F. Kulkosky
*Attorney, Agent, or Firm*—Michael B. Fein

[57] ABSTRACT

A mildew-resistant paint composition comprising a film-forming, non-wood penetrating organic polymeric paint vehicle; an isothiazolone mildewcide compound; and a stabilizing amount of a water insoluble organic soluble zinc compound; articles comprising a substrate coated with said paint composition; and methods of stabilizing isothiazolones in paint compositions are disclosed.

7 Claims, No Drawings

MILDEW RESISTANT PAINT COMPOSITIONS COMPRISING AN ISOTHIAZOLONE AND A WATER-INSOLUBLE ZINC COMPOUND, ARTICLES, AND METHODS

This is a continuation of application Ser. No. 360,504, filed Jun. 2, 1989 now abandoned.

BACKGROUND OF THE INVENTION

1. Field of the Invention

This invention relates to mildew resistant paint compositions comprising isothiazolone compounds.

2. Description of the Prior Art

Isothiazolones are well known mildewcides for film forming compositions. Isothiazolones are generally unstable without the addition of a stabilizer. In aqueous paint formulations, zinc oxide is a well known stabilizer for isothiazolones. The zinc oxide also acts as a synergist with the isothiazolones for mildew resistance in aqueous paint formulations. One problem with zinc oxide as a stabilizer is that it must be used in high concentrations, usually about 50,000 ppm of zinc oxide based on the paint formulations. Other metal salts have also been used as stabilizers for isothiazolones in mildew resistant paint compositions, but some compositions, e.g., those with copper, are highly colored.

SUMMARY OF THE INVENTION

It is therefore an object of the present invention to provide a mildew-resistant paint composition which avoids the potential color problems of previous metal salt stabilizers and is effectively stabilized with lower concentrations of metal salt stabilizers than required with zinc oxide pigments.

These objects, and other as will become apparent from the following description, are achieved by the present invention which comprises a mildew-resistant paint composition comprising a film-forming, non-wood penetrating, organic polymeric paint vehicle; an isothiazolone of the formula:

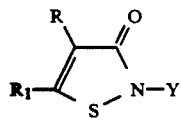

wherein Y is substituted or unsubstituted alkyl, unsubstituted or halo substituted alkenyl or alkynyl, unsubstituted or substituted cycloalkyl, unsubstituted or substituted aralkyl, or hydrogen, R is hydrogen, chloro, or methyl, and $R_1$ is hydrogen or methyl; and a stabilizing amount of a water-insoluble, organic solvent-soluble zinc compound. In another aspect, the invention comprises an article comprising a substrate coated with the mildew resistant film composition.

In yet another aspect, the invention comprises a method of imparting mildew resistance to a coating composition comprising an isothiazolone mildewcide which comprises incorporating about 1,000 to 10,000 ppm of an oil soluble zinc compound.

DETAILED DESCRIPTION OF THE INVENTION AND THE PREFERRED EMBODIMENTS

The isothiazolones useful in the invention are well known and are described in U.S. Pat. Nos. 3,523,121 and 3,761,488. A highly preferred isothiazolone is 2-octyl-3-isothiazolone. It has been found that some chlorinated isothiazolones are not stabilized by the oil soluble zinc compounds used in this invention.

The oil soluble zinc compounds useful in the paint compositions, articles and methods of this invention are zinc salts of organic carboxylic acids which are water insoluble and organic solvent soluble, i.e., oil soluble. Preferred zinc compounds are zinc salts of organic carboxylic acids, and the preferred zinc compound is zinc octoate; "octoate" is a commonly used term which is equivalent to 2-ethylhexanoate. Others which are suitable are zinc hexanoate, heptanoate, decanoate, dodecanoate, dodecenoate, cyclohexylcarboxylate, tetrahydrobenzoate, naphthenate, 2-ethylhexanoate, neodecanoate, oleate, benzoate, alkanoate (mixture of about ($C_7$–$C_{13}$) alkyl carboxylates), salts of disproportionated rosin acid, 2-phenylethanoate, and the like.

Solvents may be used to dissolve the isothiazolones and may be any organic solvent which is miscible with the isothiazolones, is compatible with the proposed end use, does not destabilize the isothiazolone, and does not react with the zinc salt to eliminate its stabilizing action.

Hydroxylic solvents, for example, polyols, such as glycols, monoethers of glycols, alcohols, and the like, may be used. An hydroxylic coalescent, such as Texanol (trimethyl-1,3-pentanediol monoisobutyrate) also may be used. In certain formulations, hydrocarbons, either aliphatic or aromatic, are useful solvents. Typical solvents are dipropylene glycol, dipropylene glycol monoethyl ether, xylene, mineral spirits, and the like. Solvents may be used in admixture as long as the zinc salt remains soluble or is well dispersed enough so as to be added conveniently and uniformly to the test formulation.

The amounts of zinc salt employed will vary depending on use conditions and concentrations of the isothiazolone in the mixture. In more concentrated solutions, effective amounts of zinc salt based on isothiazolone are in the ratios of from about 1:50 to about 2:1. Obviously higher amounts may be used, but at additional cost. At high levels of dilution of the isothiazolone (such as from 1 to 2 percent isothiazolone in the solvent), the ratio of stabilizer to isothiazolone can range from about 1:10 to about 3:1.

Other salt stabilizers such as those described in U.S. Pat. Nos. 3,870,795; 4,067,878; 4,150,026 and 4,241,214 can also be included.

Because the preferred isothiazolones and the stabilizers of the present invention are both organic-soluble and water-insoluble, they may be used in aqueous dispersions or latices, as both will diffuse into the organic polymer and be efficacious when the polymer is isolated by drying of the latex to form a film. The preferred isothiazolones and stabilizers of the present invention may also be used in oil or alkyd paint formulations.

It is known in the art that the performance of biocides can frequently be enhanced by combination with one or more other biocides. In fact, there have been numerous examples of synergistic combinations of biocides. Thus, other known biocides may be combined advantageously with the stabilized isothiazolones of this invention.

The isothiazolone and zinc compound may be separately blended into the paint to be stabilized or, preferably, the isothiazolone and the zinc compound, with or without organic solvent, may be precombined into a single package or solution before being added to the paint to be stabilized. The single package combination of isothiazolone, zinc compound, and optional organic solvent offers the advantage of improved control of the ratio of isothiazolone to zinc compound being added to the paint since a single operation is involved rather than the several steps involved when each ingredient is added separately; in addition, the pain formulator will require only one storage vessel for single-package formulations, rather than the several which would be required if each component were to be supplied separately; also, a one-step operation is inherently simpler than the multistep process of adding each ingredient separately where the chance for spillage or error is increased.

The following examples illustrate a few embodiments of the present invention. All percentages are by weight unless otherwise specified.

EXAMPLE 1

(Comparative)—Paint Formulation Free of Zinc Oxide

| Material | lb/50 gal | g/liter |
| --- | --- | --- |
| Natrosol 250 MHR hydroxyethyl cellulose | 1.5 | 3.6 |
| Ethylene glycol | 12.5 | 30 |
| Premix | | |
| Water | 56.0 | 134.4 |
| Tamol 960 (40%) poly(methacrylic acid) | 3.6 | 8.6 |
| Potassium tripolyphosphate | 0.75 | 1.8 |
| Triton CF-10 surfactant | 1.3 | 3.1 |
| Colloid 643 defoamer | 0.5 | 1.2 |
| Propylene glycol | 17.0 | 40.8 |
| Ti-Pure R-902 titanium dioxide | 112.5 | 270 |
| Minex 4 filler pigment | 79.7 | 191.3 |
| Icecap K filler pigment | 25.0 | 60 |
| Attagel 50 clay | 2.5 | 6 |

Let Down

The mixture is milled for 10 to 15 minutes in a Cowles Dissolver at 3800–4500 rpm and the following ingredients are then added at slower speed as follows:

| Film Forming acrylic copolymer | 153.0 | 367.1 |
| --- | --- | --- |
| Colloid 643 | 1.5 | 3.6 |
| Texanol coalescent | 4.7 | 11.3 |
| Mildewcide components | | |
| Ammonia (28%) | 1.16 | 2.8 |
| Natrosol 250 MHR (2.5%) | 53.50 | 128.4 |
| Water | 54.46 | 130.8 |
| Total | 581.17 | 1394.9 |

EXAMPLE 2

Zinc Octoate Stabilization

This example illustrates zinc octoate stabilization of the paint formulation of Example 1. The isothiazolone mildewcide from the above formulations, or a control in which no zinc octoate is present, is admixed with the paint so as to introduce a certain ppm of the zinc cation to the paint. The stabilizer is well-mixed into the paint, and the paint then heat-aged at 60° C. for 10 days. The samples, along with a room temperature control, separately shown to have retained essentially all of the active ingredient (a.i.), were extracted with a 9-fold volume excess of propylene glycol with intensive shaking for one minute and slower shaking for one hour. High-pressure liquid chromatography (Varian Model 5500 chromatograph and ultraviolet detector) was used to identify the amount of a.i. A level of a.i. above 75% retention is judged acceptable for commercial storage. Duplicate results are found on repeat samplings of the same experiment.

TABLE 1

| Concentration in Paint 2-n-octylisothiazolone ppm | Zn Octoate (ppm Zn) | Aging Results % a.i. retained |
| --- | --- | --- |
| 850 | 0 | 0, 35 |
| 850 | 240 | 49 |
| 850 | 480 | 88, 92 |

EXAMPLE 3

Comparative

Example 2 was repeated except that 4,5-dichloro-2-n-octylisothiazolone was substituted for the 2-n-octylisothiazolone. No stabilization is seen at the use levels studied.

While the invention has been described with reference to specific examples and applications, other modifications and uses for the invention will be apparent to those skilled in the art without departing from the spirit and scope of the invention.

What is claimed is:

1. Process for preventing chemical degradation of an isothiazolone of the formula:

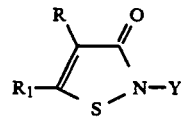

wherein Y is substituted or unsubstituted alkyl, unsubstituted or halo substituted alkenyl or alkynyl, unsubstituted or substituted cycloalkyl, unsubstituted or substituted aralkyl, or hydrogen, R is hydrogen, chloro, or methyl, and $R_1$ is hydrogen or methyl; which then mixed into a film-forming, non-wood penetrating, organic polymeric latex emulsion paint vehicle comprising mixing an effective amount of a water-insoluble, organic solvent soluble zinc salt of an organic carboxylic acid selected from the group consisting of octoate, hexanoate, heptanoate, decanoate, dodecanoate, cyclohexylcarboxylate, 2-ethylhexanoate, neodecanoate, oleate, alkanoate (mixture of about ($C_2$–$C_{13}$) alkyl carboxylates), with said isothiazolone so as to prevent chemical degradation of said isothiazolone in said latex.

2. Process of claim 1 which comprises from 0.01 to 99.9999 parts of said isothiazolone (b) and from 0.001 and 99.99 parts of said zinc compound (c).

3. Process of claim 2 which comprises form 5 to 40 parts of said isothiazolone and from 60 to 95 parts of said zinc salt.

4. Process of claim 1 which comprises from about 0.01 to about 50 parts of said isothiazolone (b); from about 0.0001 to about 10 parts of said zinc salt (c), and which further comprises from about 40 to about 99.9899 parts of a solvent.

5. Process of claim 4 which comprises from 1 to 25 parts of (b), from 0.1 to 10 parts of (c) and from 65 to 98.9 parts of the solvent.

6. Process of claim 4 wherein the solvent is chosen from the group consisting of aliphatic hydrocarbons, aromatic hydrocarbons, dihydric alcohols, and monoalkyl ethers of dihydric alcohols.

7. Process of claim 1 wherein said isothiazolone is 2-octyl-3-isothiazolone.

* * * * *

UNITED STATES PATENT AND TRADEMARK OFFICE
CERTIFICATE OF CORRECTION

PATENT NO. : 5,208,272

DATED : May 4, 1993

INVENTOR(S) : Stanley LeSota

It is certified that error appears in the above-identified patent and that said Letters Patent is hereby corrected as shown below:

Col. 4, line 45: "$(C_2-C_{13})$" should read --$(C_7-C_{13})$--

Signed and Sealed this

Twenty-sixth Day of April, 1994

Attest:

BRUCE LEHMAN

*Attesting Officer*    *Commissioner of Patents and Trademarks*